United States Patent [19]

Shepherd

[11] 4,198,522

[45] Apr. 15, 1980

[54] 4-(MONOALKYLAMINO)PHENYL CARBINOLS AND ESTER DERIVATIVES

[75] Inventor: Robert G. Shepherd, South Nyack, N.Y.

[73] Assignee: American Cyanamid Company, Stamford, Conn.

[21] Appl. No.: 836,948

[22] Filed: Sep. 27, 1977

[51] Int. Cl.² .................... C07C 91/40; C07C 93/26
[52] U.S. Cl. .................... 560/250; 260/390; 260/501.17; 260/501.18; 260/501.19; 260/509; 260/562 A; 260/570 AB; 260/571; 260/574; 424/199; 424/311; 424/315; 424/316; 424/319; 424/324; 424/330; 560/106; 560/193; 560/252; 562/441; 562/452

[58] Field of Search .................. 560/250–252; 260/519, 509, 570 AB, 574, 571, 390, 562 A, 501.17, 501.18, 501.19

[56] References Cited

U.S. PATENT DOCUMENTS

| | | | |
|---|---|---|---|
| 2,373,438 | 4/1945 | Weinmayr | 560/250 |
| 3,655,734 | 4/1972 | Richter et al. | 560/152 |

OTHER PUBLICATIONS

Chem. Abstracts, 55:9930e.

*Primary Examiner*—Vivian Garner
*Attorney, Agent, or Firm*—Edward A. Conroy, Jr.

[57] ABSTRACT

This disclosure describes 4-monoalkylaminophenyl carbinols (primary, secondary, and tertiary alcohols) and with derivatives and salts thereof useful as hypolipidemic and anti-atherosclerotic agents.

9 Claims, No Drawings

4-(MONOALKYLAMINO)PHENYL CARBINOLS AND ESTER DERIVATIVES

BRIEF SUMMARY OF THE INVENTION

This invention relates to new organic compounds and, more particularly, is concerned with novel 4-monoalkylaminophenyl carbinols (primary, secondary, and tertiary alcohols) and with derivatives and salts thereof which may be represented by the following structural formula:

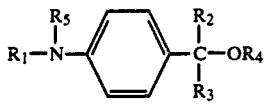

wherein $R_1$ is a straight chain or branched alkyl group of the formula $C_nH_{2n+1}$ wherein n is an integer from 8 to 19, inclusive; $R_2$ and $R_3$ are each individually selected from the group consisting of hydrogen, alkyl having up to 6 carbon atoms, phenyl, substituted phenyl, phenyl lower alkyl and substituted phenyl lower alkyl; $R_4$ is selected from the group consisting of hydrogen and alkanoyl having up to 6 carbon atoms, and $R_5$ is hydrogen or a group convertible in vivo thereinto such as methyl, ethyl, carboxymethyl, lower alkanoyl ($C_1$–$C_6$), succinyl, 1-(sodium sulfo) lower alkyl, 1-(sodium sulfo) polyhydroxyalkyl or 1,3-bis(sodium sulfo) aralkyl.

A preferred embodiment of this invention consists of those compounds in which n is an integer from 14 to 19, inclusive, namely, those of the formula:

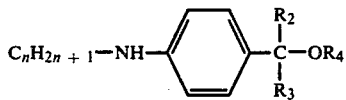

wherein $R_2$, $R_3$ and $R_4$ are as previously defined.

A more preferred embodiment of this invention consists of those compounds in which n is an integer from 14 to 19 inclusive, namely those of the formula:

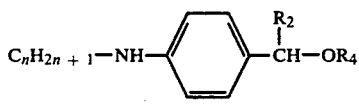

wherein $R_2$ is hydrogen or lower alkyl and $R_4$ is as previously defined.

The straight chain alkyl groups for the substituent $R_1$ may be, for example, octyl, nonyl, decyl, undecyl, dodecyl, tridecyl, tetradecyl, pentadecyl, hexadecyl, heptadecyl, octadecyl and nonadecyl. Suitable branched alkyl groups for the substituent $R_1$ may be, for example, 1-methylpentadecyl, 1-ethyltetradecyl, 1-heptylnonyl, 2-ethyldodecyl, 1,4-diethyloctyl, 11-methyldodecyl, 5,5-dimethylhexyl, 4,8,12-trimethyltridecyl, 2,4,6,8-tetramethylnonyl, 1,4-dimethyl-1-ethylhexyl, 15-methylhexadecyl, 14-methylpentadecyl, 13,13-dimethyltetradecyl, 15,15-dimethylhexadexyl, and the like. Suitable lower alkyl and lower alkoxy groups contemplated by this invention are those having up to 6 carbon atoms, as for example, methyl, ethyl, isopropyl, propyl, tert-butyl; methoxy, ethoxy, isobutoxy, n-amyloxy, and the like. Suitable phenyl and substituted phenyl groups include, for example, phenyl, 4-lower alkoxyphenyl, 2,4-di-loweralkoxyphenyl, 4-carboxyphenyl, 4-(sodium sulfo)phenyl, 4-(carboxymethoxy)phenyl, 4-loweralkylphenyl, 2,4-di-loweralkylphenyl, 4-(carboxymethyl)phenyl, etc. Suitable phenyl lower alkyl and substituted phenyl lower alkyl groups include, for example, benzyl, α-phenylethyl, β-phenylethyl, and substituted benzyl such as 4-loweralkoxybenzyl, 2,4-di-loweralkoxybenzyl, 4-carboxybenzyl, 4-sulfobenzyl, 4-(carboxymethoxy)benzyl, 4-loweralkylbenzyl, 2,4-di-lower alkylbenzyl, 4-(carboxymethyl)benzyl, etc.

The invention also pertains to novel compositions of matter useful as anti-atherosclerotic agents and to methods of meliorating atherosclerosis by counteracting hyperlipemia and arterial plaque formation in mammals therewith; the active ingredients of said compositions of matter being the novel 4-(monoalkylamino)phenyl carbinols (primary, secondary and tertiary alcohols) of the present invention as the free alcohol or in the derivatized form or in the form of a pharmaceutically acceptable salt with an organic or inorganic acid or base. The invention also contemplates a method for lowering serum lipids and for meliorating atherosclerosis in mammals by the administration of said alcohols.

BACKGROUND OF THE INVENTION

Considerable effort has been directed in recent years to obtain substances useful in counteracting the consequences of hyperlipidemia, a condition involving elevated cholesterol, phospholipid and/or triglyceride levels in the blood, and of hyperlipoproteinemia, involving an imbalance of the lipoproteins. The most serious condition associated with hyperlipidemia and hyperlipoproteinemia is atherosclerosis, a form of arteriosclerosis characterized by lipid accumulation and thickening of the walls of both medium-sized and large arteries such as the aorta. Their walls are thereby weakened and the elasticity and effective internal size of the arteries decreased. Atherosclerosis, the most common cause of coronary artery disease, is of great medical importance since it tends to occlude those arteries supplying blood to the heart muscles and brain, thereby producing permanent damage to these organs. Such damage may lead to congestive heart failure, life-threatening arrhythmias, senility, or stroke. Involvement of leg arteries may lead to gangrene and loss of the limb. It has been known for more than 100 years that cholesterol is a major component of atherosclerotic lesions or plaques. Investigators have been trying to determine the role of cholesterol in their initiation and development and also, most importantly, whether lesion formation can be prevented or reversed and enlargement of lesions be slowed or stopped. The earliest lesions are known to be fatty streaks, largely of cholesterol, which often progress in stages to plaques containing cellular, fibrous and calcified material in addition to the lipids.

The evidence that hyperlipidemia is one of the factors involved in coronary heart disease is very impressive. A most important study carried out in Framingham, Mass. (Gordon & Verter, 1969) in over 5,000 persons for more than 12 years established a correlation between high concentrations of blood cholesterol and increased risk of heart attack. Although the causes of coronary artery disease are multiple, one of the most constant factors has been the elevated concentration of lipids in the blood plasma. A combined elevation of cholesterol and triglycerides has been shown (Carlson & Bottiger, 1972) to carry the highest risk of coronary heart disease. The majority of patients with ischemic heart disease or peripheral vascular disease were found to have hyperlipoproteinemia, involving very low-density and/or low-density lipoproteins (Lewis et al. 1974).

The reason for most treatment of hyperlipidemia or hyperlipoproteinemia is for arresting, reversing or preventing atherosclerosis. In the past, attempts have been made to lower the levels of cholesterol, phospholipids, and triglycerides in the blood by the oral feeding of various substances which have been generally referred to in the art as hypolipidemic agents or hypocholesteremic adjuvants. Typical of such substances are lecithin, pectin, cottonseed oil, and the mucilaginous substances listed in U.S. Pat. No. 3,148,114. In addition, several synthetic hypolipidemic agents are now available, namely, clofibrate, D-thyroxine, cholestyramine and nicotinic acid [(Levy & Frederickson, Postgraduate Medicine 47, 130 (1970)]. Clofibrate has the undesirable side-effect of causing hypertrophy of the liver in some patients.

The development of agents capable of reducing elevated blood lipids and of favorably altering blood-lipoprotein patterns is considered by medical authorities to be extremely important for the treatment and prevention of atherosclerosis. Orally active agents are required since patients usually take them for a number of years.

DETAILED DESCRIPTION OF THE INVENTION

U.S. Pat. No. 3,868,416 discloses and claims certain 4-(monoalkylamino)benzoic acids, esters, pharmaceutically acceptable salts, pharmaceutical compositions thereof and a method of lowering serum lipid levels in mammals therewith. No prior art is known which discloses the 4-(monoalkylamino)-phenyl carbinols (primary, secondary and tertiary alcohols) and derivatives and salts thereof of this invention and no hypolipidemic activity has been reported in the literature for these compounds and they are different in structure from other hypolipidemic agents. The compounds of this invention lower serum-lipid concentrations and also minimize atheroma formation in the aorta. These 4-(monoalkylamino)phenyl carbinols provide the oral administration required of hypolipidemic agents, which patients usually take for many years. The anti-atherogenic activity of the alkylaminobenzoic acids mentioned above has been announced; Abstract No. 27, American Oil Chemists Society, 67th Meeting, New Orleans, April 21-24, 1876; Federation Proceedings 36, Abstract No. 4706 (1977).

We have now found that the members of this class of compounds can safely and effectively lower serum lipids in warm-blooded animals. For some time it has been considered desirable to lower serum lipid levels and to correct lipoprotein imbalance in mammals as a preventive measure against atherosclerosis. The compounds of the present invention do not act by blocking late stages of cholesterol biosynthesis and thus do not produce accumulation of intermediates such as desmosterol, as equally undesirable as cholesterol itself. Compounds with the combination of therapeutically favorable characteristics possessed by those of the present invention can be safely administered to warm blooded mammals for the treatment of hyperlipidemic and atherosclerotic states found in patients with or prone to heart attacks, to peripheral or cerebral vascular disease, and to stroke.

The 4-(monoalkylamino)phenyl carbinols (primary, secondary and tertiary alcohols) of the present invention are, in general, white crystalline solids having characteristic melting points and spectral characteristics. They are soluble in organic solvents such as lower alkanols, chloroform, benzene, dimethylformamide, and the like, but are generally insoluble in water.

The novel compounds of the present invention form non-toxic acid-addition salts with a variety of pharmacologically acceptable organic and inorganic salt-forming reagents. Thus, acid-addition salts, formed by admixture of the organic free base with one or more equivalents of an acid, suitably in a neutral solvent, are formed with such acids as sulfuric, phosphoric, hydrochloric, hydrobromic, and the like. The acid-addition salts of the organic bases of the present invention are, in general, crystalline solids. In addition, those compounds wherein $R_2$ and/or $R_3$ contain acidic groups form pharmaceutically acceptable cationic salts with bases such as the alkali metal hydroxides, alkaline earth metal hydroxides, and the like.

The free alcohols of this invention may be prepared from 4-aminophenylcarbinols, 0-alkanoyl esters thereof, 4-alkylaminobenzoic acids, esters thereof, and from 4-alkylaminobenzaldehydes or adducts thereof.

The benzyl alcohols (primary carbinols) are generally prepared by metal hydride reduction of the 4-monoalkylaminobenzoic acids or esters thereof in a suitable solvent such as tetrahydrofuran or diethyl ether at 10°-50° C. over a period of time consisting of 1-12 hours. Generally ambient temperature is preferred. After destruction of the excess hydride the product is isolated directly or indirectly by extraction. The product is purified by recrystallization from organic solvents such as the hexanes, cyclohexane and the like. The metal hydrides consist of lithium aluminum hydride and lithium borohydride. The reduction of the 4-monoalkylaminobenzoic acid or esters thereof may also be carried out with diborane ($B_2H_6$).

The 4-monoalkylaminobenzoic acid esters may also be reduced to the corresponding benzyl alcohols by a chemical method employing sodium in ethanol (the Bouveault-Blanc reaction) or by a catalytic hydrogenation method using copper chromite catalyst at an elevated temperature and high pressure.

The primary and secondary α-substituted-(alkyl and aryl) benzyl alcohols are prepared from the corresponding aldehydes or ketones by reaction with alkyl lithium or aryl lithium in a suitable solvent such as dimethoxyethane at 10°-50° C. for 10 minutes up to 2 hours, quenching the reaction therefrom, and extracting the product with a chlorinated hydrocarbon such as dichloromethane. The product is purified by recrystallization from an organic solvent such as the hexanes, methyl cyclohexanes, and the like.

The secondary and tertiary alcohols of this invention may also be prepared by the classical Grignard reaction with reagents such as alkyl-Mg-halogen, aryl-Mg-halogen on the corresponding aldehydes and ketones in suitable solvents such as diethylether and tetrahydrofuran. The reaction mixtures are generally treated with a reagent such as aqueous ammonium chloride, and the product therefrom is isolated and purified by extraction and recrystallization.

The 4-alkylaminophenylcarbinols of this invention are also prepared from the 4-aminophenyl primary, secondary or tertiary carbinols by alkylations employing alkyl halides, sulfates, tosylates, or mesylates with or without solvent at 50°-150° C. using an excess of the aminophenylcarbinol as base or an equivalent of an organic or inorganic base. The 0-alkanoyl derivatives of the aminophenylcarbinols may be alkylated similarly. Alternative methods of preparation are (a) by reductive alkylation of the various types of 4-aminophenylcarbinols with suitable carbonylalkanes, and (b) by diborane reduction of 4-alkanoylaminophenylcarbinols. The reductive alkylation may also be carried out on 4-aminobenzaldehyde and derivatives or on 4-aminoacetophenone and other phenones in which case the carbonyl group of these substrates is simultaneously reduced. Similarly, 4-alkanoylaminobenzaldehydes and derivatives or 4-alkanoylaminoacetophenones and other phenones are subjected to simultaneous or stepwise reduction of the anilide and the phenone carbonyl groups.

The secondary alcohols of this invention may also be prepared by chemical and catalytic reduction of the corresponding aminoalkylaminoacetophenones and monoalkylaminobenzophenones. The chemical methods employ e.g. sodium and alcohol, sodium borohydride, and the like. The catalytic methods employed e.g. nickel catalysts in ethanol, and the like.

The 4-monoalkylaminobenzyl alcohol N,O-diacylates can be prepared by acylation of the 4-monoalkylaminobenzyl alcohols with acyl halides or anhydrides such as acetyl chloride, acetic anhydride, benzoyl chloride, benzoic anhydride, succinic anhydride, etc. in the presence of a suitable base as pyridine, triethylamine and the like with or without an organic solvent.

The N-alkanoyl-4-monoalkylaminobenzyl alcohols can be prepared by treatment of the N,O-dialkanoates with a base such as potassium hydroxide in an alcoholic solvent such as methanol, ethanol and the like. The reaction is carried out at ambient temperature up to the temperature of reflux of the alcohol employed. The reaction time is from 30 minutes up to 6 hours.

The 4-monoalkylaminobenzyl alcohol O-acylates can be prepared generally as follows. Acetyl bromide is added to a solution of the free benzyl alcohol in an acidic solvent such as trifluoroacetic acid, and the mixture is stirred for a short time (15 min. to 2 hours). Water is added, and the solution is evaporated in vacuo. The residue is treated with diethylether to provide the O-acylates in the form of their hydrobromide salt. Treatment of the latter with alkali organic salts such as sodium acetate generates the 4-monoalkylaminobenzyl alcohol O-acylates.

Certain derivatives

of the aminobenzoyl nitrogen atom are useful for providing greater solubility, more uniform and reliable intestinal absorption, and for a certain degree of modification of the pharmacology of the compounds of the present invention. Some of these derivatives can be converted to the corresponding N-H forms by the acidity of the stomach or the alkalinity of the small intestine. Others are converted by metabolic processes. The methyl and carboxymethyl derivatives and the like are prepared by the alkylation, reductive alkylation, and acylamino reduction methods above. Derivatives such as the acetyl and succinyl compounds may be prepared using acetyl chloride, acetic anhydride, succinic anhydride, etc. in the presence of pyridine, triethylamine or the like at temperatures moderate enough to avoid acylation of the amide moiety. The 1-(sodium sulfo)-alkyl derivatives are obtained by reaction of the 4-(monoalkylamino)benzamides, or suitable intermediates in certain cases, with sodium bisulfite and an aliphatic aldehyde, a polyhydroxyaldehyde such as glyceraldehyde or glucose, or cinnamaldehyde in a mixed organic-aqueous medium. In the case of cinnamaldehyde, the di-sulfonate salts result from addition of the bisulfite to the carbon-nitrogen double bond of the anil intermediate as well as to the carbon-carbon double bond of cinnamaldehyde itself.

The novel compounds of the present invention are not only hypolipidemic agents but also prevent or diminish the formation or enlargement of arterial plaques in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 grams to about 7.0 grams of the active compound for a subject of about 70 kg. of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compound may be administered conveniently by the oral route. It is not known how these novel compounds operate in the blood serum and no theory of why these compounds so operate is advanced. It is not intended that the present invention should be limited to any particular mechanism of action of lowering serum lipids or of meliorating atherosclerosis, or be limited to compounds acting by only one mechanism.

The compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: A binder such as gum tragacanth, acacia, corn starch or gelatin; excipients such as dicalcium phosphate, a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When tne dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active ingredients may be incorporated into sustained-release preparations and formulations.

The invention will be described in greater detail in conjunction with the following specific examples.

EXAMPLE 1 p-Hexadecylaminobenzyl Alcohol

A. From methyl p-hexadecylaminobenzoate

Methyl p-hexadecylaminobenzoate (1 g.) is partially dissolved at room temperature in tetrahydrofuran (10 ml.). To this is added portionwise an excess of lithium aluminum hydride (0.5 g.), and the reaction mixture is stirred at room temperature for a total of 2 hours. The mixture is treated with excess 10% aqueous ammonium chloride, and then filtered through diatomaceous earth. Evaporation in vacuo of the filtrate gives a solid residue, wt. 0.68 g. Recrystallization from hexanes gives the product of the Example as white crystals, m.p. 74°–75° C.

B. From p-Hexadecylaminobenzoic acid p-Hexadecylaminobenzoic acid (2.0 g.) is dissolved in 20 ml. of dry tetrahydrofuran, and to this is added portionwise at room-temperature 0.5 g. of lithium aluminum hydride. The mixture is stirred at room temperature for 3 hours, and then is quenched with 10% aqueous ammonium chloride solution. The mixture is filtered, and the filtrate is evaporated in vacuo to provide a yellow solid. The residue is extracted several times with methylene chloride and the extracts are evaporated in vacuo to give a white solid. Recrystallization from hexane gave the product of the Example, m.p. 74°–75° C. Replacement of p-hexadecylaminobenzoic acid with p-octylaminobenzoic acid, p-nonylaminobenzoic acid, p-decylaminobenzoic acid, p-undecylaminobenzoic acid, p-dodecylaminobenzoic acid, p-tridecylaminobenzoic acid, p-(14-methylpentadecyl)aminobenzoic acid, p-pentadecylaminobenzoic acid, p-heptadecylaminobenzoic acid, p-octadecylaminobenzoic acid, and nondecylaminobenzoic acid provide respectively, p-octylaminobenzyl alcohol, p-nonylaminobenzyl alcohol, p-decylaminobenzyl alcohol, p-undecylaminobenzyl alcohol, p-dodecylaminobenzyl alcohol, p-tridecylaminobenzyl alcohol, p-pentadecylaminobenzyl alcohol, p-(14-methylpentadecyl)aminobenzyl alcohol, p-heptadecylaminobenzyl alcohol, p-octadecylaminobenzyl alcohol and p-nonadecylaminobenzyl alcohol.

EXAMPLE 2 p-Hexadecylaminobenzyl Alcohol Hydrochloride

Hydrogen chloride is bubbled with stirring into a solution of p-hexadecylaminobenzyl alcohol (1.0 g.) in anhydrous diethyl ether (50 ml.). Immediately a white precipitate forms, and after 3 minutes the mixture is filtered and washed several times with anhydrous diethyl ether to provide the product of the Example as a white solid (1.0 g.), m.p. shrinkage at 70° C., and gradual decomposition up to about 160° C.

EXAMPLE 3 p-Hexadecylaminobenzyl Alcohol Hydrobromide

Following the procedure of Example 2, employing 0.5 ml. of 48% hydrobromic acid provides the salt.

EXAMPLE 4

N-Hexadecyl-α-hydroxy-p-acetotoluidide Acetate p-Hexadecylaminobenzyl alcohol (150 mg.) in pyridine (1 ml.) is treated with acetic anhydride (0.5 ml.) and the mixture is allowed to stand at room temperature for 3 hours. It is then poured into cold-water providing a gum which rapidly changes into a white solid. This is collected by filtration, washed with water and dried. This provides 170 mg. of the product of the Example m.p. 54°–56° C. Infrared spectral analysis confirms the acetylation of both the oxygen and nitrogen sites.

EXAMPLE 5

N-Hexadecyl-α-hydroxy-p-acetotoluidide

N-hexadecyl-α-hydroxy-p-acetotolidide acetate (2.0 g.) in methanol (25 ml.) is refluxed with 3 ml. of 2 N potassium hydroxide in methanol for 2 hours. Solvent is removed in vacuo, water added, and the white residue is collected by filtration. The solid is dissolved in methylene chloride, the resulting solution dried over anhydrous magnesium sulfate, filtered, and evaporated. The product of the Example is thus obtained as a white solid, m.p. 73°–75° C.

EXAMPLE 6 p-Hexadecylaminobenzyl Acetate Hydrobromide

Acetyl bromide (0.33 ml.) is added to a solution of p-hexadecylaminobenzyl alcohol (1.0 g.) in trifluoroacetic acid (5 ml.), and the solution is stirred at room temperature for 0.5 hours. Two drops of water are added, and the solution is stirred at room temperature for 0.5 hours. Two drops of water are added, and the solution is evaporated in vacuo. The residue is dissolved in hexanes, and re-evaporated. The residue is treated with anhydrous diethyl ether, and the white solid is collected by filtration, washed with anhydrous diethyl ether, and dried to give 1.01 g. of the product of the Example, m.p. 80°–82° C.

EXAMPLE 7 p-Hexadecylaminobenzyl Acetate

One-half ml. of 30% aqueous sodium acetate is added to a solution of p-hexadecylaminobenzyl alcohol acetate hydrobromide (100 mg.) in methylene chloride (2 ml.). After thorough mixing, the organic layer is separated, dried over anhydrous sodium sulfate, and evaporated at ambient temperature to provide the product (50 mg.) of the Example, m.p. 43°–45° C.

EXAMPLE 8 p-Heptadecylaminobenzyl Acetate Hydrobromide

Replacement of p-hexadecylaminobenzyl alcohol in Example 6 with p-heptadecylaminobenzyl alcohol gives the product of the Example.

EXAMPLE 9

N-Tetradecyl-α-hydroxy-p-acetotoluidide Acetate

Replacement of p-hexadecylaminobenzyl alcohol in Example 4 with p-tetradecylaminobenzyl alcohol gives the product of the Example.

EXAMPLE 10 p-Tetradecylaminobenzyl Acetate Hydrobromide

Replacement of p-hexadecylaminobenzyl alcohol in Example 6 with p-tetradecylaminobenzyl alcohol gives the product of the Example.

EXAMPLE 11 p-Tetradecylaminobenzyl Acetate

Replacement of p-hexadecylaminobenzyl alcohol acetate hydrobromide in Example 7 with p-tetradecylaminobenzyl alcohol acetate hydrobromide gives the product of the Example.

EXAMPLE 12 p-(1-Methylundecylamino)benzyl Alcohol

Replacement of p-hexadecylaminobenzoic acid and its methyl ester in Example 1 with p-(1-methylundecylamino)-benzoic acid gives the product of the Example.

EXAMPLE 13 p-Hexadecylamino-α-methylbenzyl Alcohol p-Aminobenzonitrile (11.8 g., 0.1 mole) and 1-bromohexadecane (15.25 g., 0.05 mole) are dissolved in hexamethylphosphoramide (200 ml.) and heated under nitrogen in an oil bath maintained at 120° C. for 22 hours. The reaction mixture is cooled to room-temperature, and water (50 ml.) is added gradually. The mixtue is then chilled in an ice-bath. The precipitate separated is filtered, washed thoroughly with water and dried. It is then washed repeatedly with hexane and dried, providing 14.2 g. of a pale brownish yellow granular solid as a homogeneous product. Recrystallization from ether-hexane affords p-hexadecylaminobenzonitrile as pale yellow prisms, m.p. 63°-64° C.

Di-isobutylaluminum hydride (54 ml., 25% solution in toluene) is added with stirring to a solution of p-hexadecylaminobenzonitrile (11.4 g.) under a nitrogen atmosphere. The temperature rises to 40° C. during the addition which takes 30 minutes, and the reaction is then stirred for 1 hour. A solution of methanol in toluene (50 ml., 1:1) is added over 30 minutes, and the mixture is poured into vigorously stirred ice-cold aqueous sulfuric acid (500 ml., 5%). After 10 minutes diatomaceous earth (30 g.) is added, the mixture filtered and the organic layer separated. The aqueous solution is extracted twice with toluene (100 ml.) and the combined organic layers are washed with aqueous sodium bicarbonate, dried over magnesium sulfate, decolorized with charcoal, filtered and evaporated in vacuo to give a light yellow crystalline solid. The crude product is dissolved in dichloromethane and filtered through magnesium silicate (80 g.) to give a white crystalline material on removal of the solvent. The solid is recrystallized from dichloromethane-hexanes giving p-hexadecylamino benzaldehyde as colorless fine needles (6.0 g.), m.p. 84°-85° C.

p-Hexadecylaminobenzaldehyde (5.0 g.) is dissolved in dimethoxyethane (100 ml.) under nitrogen. Methyl lithium (1.5 M solution in ether, 30 ml.) is then added with stirring over 10 minutes. After an additional 15 minutes, water (30 ml.) is added to quench the reaction. The solution is then diluted with dichloromethane (250 ml.) and washed three times with water. The organic layer is dried over magnesium sulfate, filtered through hydrated magnesium silicate and the solvents removed in vacuo to give a yellow solid. Recrystallization from hexanes gives the product of the Example, m.p. 55°-56° C.

The product of the Example is also prepared by use of methyl magnesium bromide in place of methyl lithium. The reaction is carried out in diethyl ether or tetrahydrofuran with subsequent quenching of the reaction with ammonium chloride.

EXAMPLE 14 p-Hexadecylamino-α-phenylbenzyl Alcohol

Following the procedure of Example 13 employing phenyl lithium or phenyl magnesium bromide provides the product of the Example.

EXAMPLE 15 p-Hexadecylamino-α,α-dimethylbenzyl Alcohol p-Aminoacetophenone (87.6 g.) is heated with hexadecylbromide (198 g.) in dry hexamethylphosphoramide (300 ml.) containing anhydrous potassium carbonate (90 g.) for 16 hours at 100° C. The solution is cooled to room temperature, filtered to remove solids, and the filtrate is diluted with cold water (20 ml.). The amber solid so obtained is collected and washed with water. Recrystallization from ethanol followed by dichloromethane provides p-hexadecylaminoacetophenone.

Following the procedures of Example 13 employing p-hexadecylaminoacetophenone provides the product of the Example.

EXAMPLE 16 p-Hexadecylamino-α-methyl, α-phenylbenzyl Alcohol

Following the procedure of Example 13 reaction of p-hexadecylaminoacetophenone with phenyl lithium, or phenyl magnesium bromide provides the product of the Example.

EXAMPLE 17 p-Hexadecylamino-α,αdiphenylbenzyl Alcohol

Following the procedure of Example 15 employing p-aminobenzophenone provides p-hexadecylaminobenzophenone.

Following the procedure of Example 13 reaction of p-hexadecylaminobenzophenone with phenyl lithium or phenyl magnesium bromide provides the product of the Example.

EXAMPLE 18 p-Hexadecylamino-α-methylbenzyl Alcohol Hydrochloride

Following the procedure of Example 2 employing p-hexadecylamino-α-methylbenzyl alcohol provides the product of the Example.

EXAMPLE 19 p-Hexadecylamino-α-methylbenzyl Acetate Hydrobromide

Following the procedure of Example 6 employing p-hexadecylamino-α-methylbenzyl alcohol provides the product of the Example.

EXAMPLE 20 p-Hexadecylamino-α-methylbenzyl Acetate

Following the procedure of Example 7 employing p-hexadecylamino-α-methylbenzyl alcohol acetate hydrobromide provides the product of the Example.

EXAMPLE 21

N-Hexadecyl-4'-(1-hydroxyethyl)acetanilide Acetate

Following the procedure of Example 4 employing p-hexadecylamino-α-methylbenzyl alcohol provides the product of the Example.

EXAMPLE 22

N-Hexadecyl-4'-(1-hydroxyethyl)acetanilide

Following the procedure of Example 5 employing N-hexadecyl-4'-(1-hydroxyethyl)acetanilide acetate provides the product of the Example.

EXAMPLE 23

N-Hexadecyl-4'-(1-hydroxy-1-methylethyl)-acetanilide Acetate

Following the procedure of Example 4 employing p-hexadecylamino-α,α-dimethylbenzyl alcohol provides the product of the Example.

EXAMPLE 24

| Preparation of 50 mg. Tablets | | |
|---|---|---|
| Per Tablet | | Per 10,000 Tablets |
| 0.050 gm. | Active ingredient | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | | 15 gm. |
| 0.150 gm. | | 1490 gm. |

The active ingredient, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 25

| Preparation of Oral Suspension | |
|---|---|
| Ingredient | Amount |
| Active ingredient | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water    qs ad | 100 ml. |

The sorbitol solution is added to 40 ml. of distilled water and the active ingredient is suspended therein. The saccharin, sodium benzoate, flavor and dye are added and dissolved. The volume is adjusted to 100 ml. with distilled water. Each ml. of syrup contains 5 mg of active ingredient.

I claim:

1. p-Normal-alkyl ($C_8$–$C_{19}$) aminobenzyl alcohols of the formula:

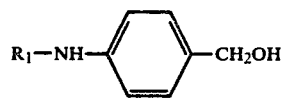

wherein $R_1$ is a straight chain alkyl group having 8–19 carbon atoms.

2. Lower alkanoyl ($C_1$–$C_6$) esters of p-normal alkyl ($C_8$–$C_{19}$) aminobenzyl alcohols of the formula:

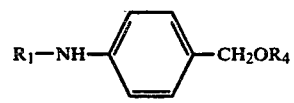

wherein $R_1$ is a straight chain alkyl group having 8–19 carbon atoms and $R_4$ is lower alkanoyl having 1–6 carbon atoms.

3. Lower alkanoyl ($C_1$–$C_6$) esters of p-branched chain alkyl ($C_8$–$C_{19}$) aminobenzyl alcohols of the formula:

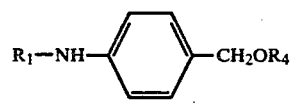

wherein $R_1$ is a branched chain alkyl group having 8–19 carbon atoms and $R_4$ is lower alkanoyl having 1–6 carbon atoms.

4. p-Hexadecylaminobenzyl alcohol.
5. p-Hexadecylaminobenzyl alcohol hydrochloride.
6. p-Hexadecylaminobenzyl acetate.
7. p-(14-Methyl pentadecyl)amino benzyl alcohol.
8. p-Hexadecylamino-α-methylbenzyl alcohol.
9. p-Branched chain alkyl ($C_8$–$C_{19}$) aminobenzyl alcohols of the formula:

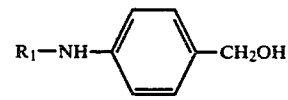

wherein $R_1$ is a branched chain alkyl group having 8–19 carbon atoms.